US00PP17210P3

(12) United States Plant Patent
Kataoka

(10) Patent No.: US PP17,210 P3
(45) Date of Patent: Nov. 14, 2006

(54) ***GAURA LINDHEIMERII* PLANT NAMED 'GAUHEHA'**

(50) Latin Name: *Gaura lindheimeri*
Varietal Denomination: Gauheha

(75) Inventor: Michio Kataoka, Niitsu (JP)

(73) Assignee: Nichien Co., Ltd. (JP)

( * ) Notice: Subject to any disclaimer, the term of this patent is extended or adjusted under 35 U.S.C. 154(b) by 22 days.

(21) Appl. No.: 10/980,470

(22) Filed: Nov. 3, 2004

(65) Prior Publication Data

US 2006/0095995 P1 May 4, 2006

(51) Int. Cl.
*A01H 5/00* (2006.01)

(52) U.S. Cl. ..... Plt./263

(58) Field of Classification Search ..... Plt./263, Plt./226

See application file for complete search history.

*Primary Examiner*—Kent Bell
(74) *Attorney, Agent, or Firm*—The Webb Law Firm

(57) ABSTRACT

A new and distinct *Gaura lindheimeri* plant with red-purple colored flowers, attractive variegated foliage, and a long blooming season.

4 Drawing Sheets

Botanical classification: *Gaura lindheimeri.*
Varietal denomination: *'Gauheha'*

BACKGROUND OF THE INVENTION

The present invention comprises a new and distinct cultivar of *Gaura lindheimeri* known by the varietal name 'Gauheha'. The new variety was discovered and isolated in Niigata, Japan in May of 2002 as a naturally occurring branch mutation of *Gaura lindheimeri* 'Gauchebra' (U.S. Plant Pat. No. 14,581). The new variety exhibits similar flower color and flower habit to 'Gauchebra', but is different from 'Gauchebra' in the coloring of the foliage. The flower color, plant habit and foliage color of 'Gauheha' differ from other *Gaura lindheimeri* varieties known to the breeder. The new variety was first asexually reproduced by terminal cuttings in Niigata, Japan. The new variety has been trial and field tested and has been found to retain its distinctive characteristics and remain true to type through successive asexual propagations.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
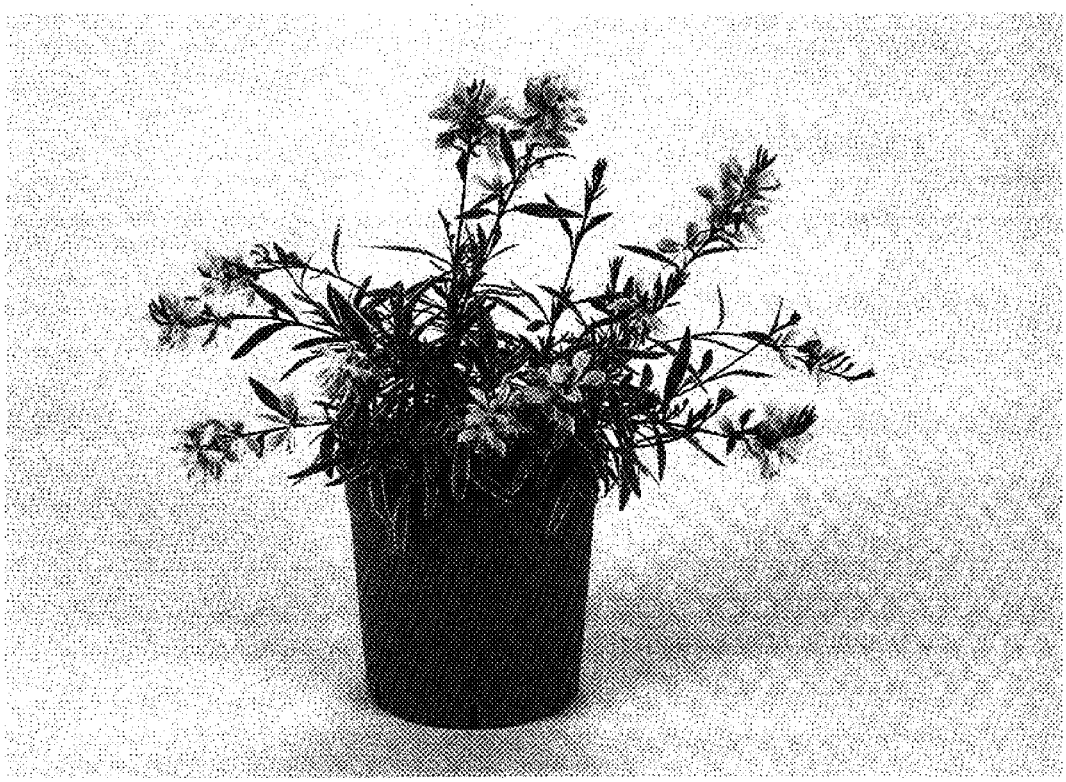
FIG. 1 is a photograph of the new variety.
Figure 2:
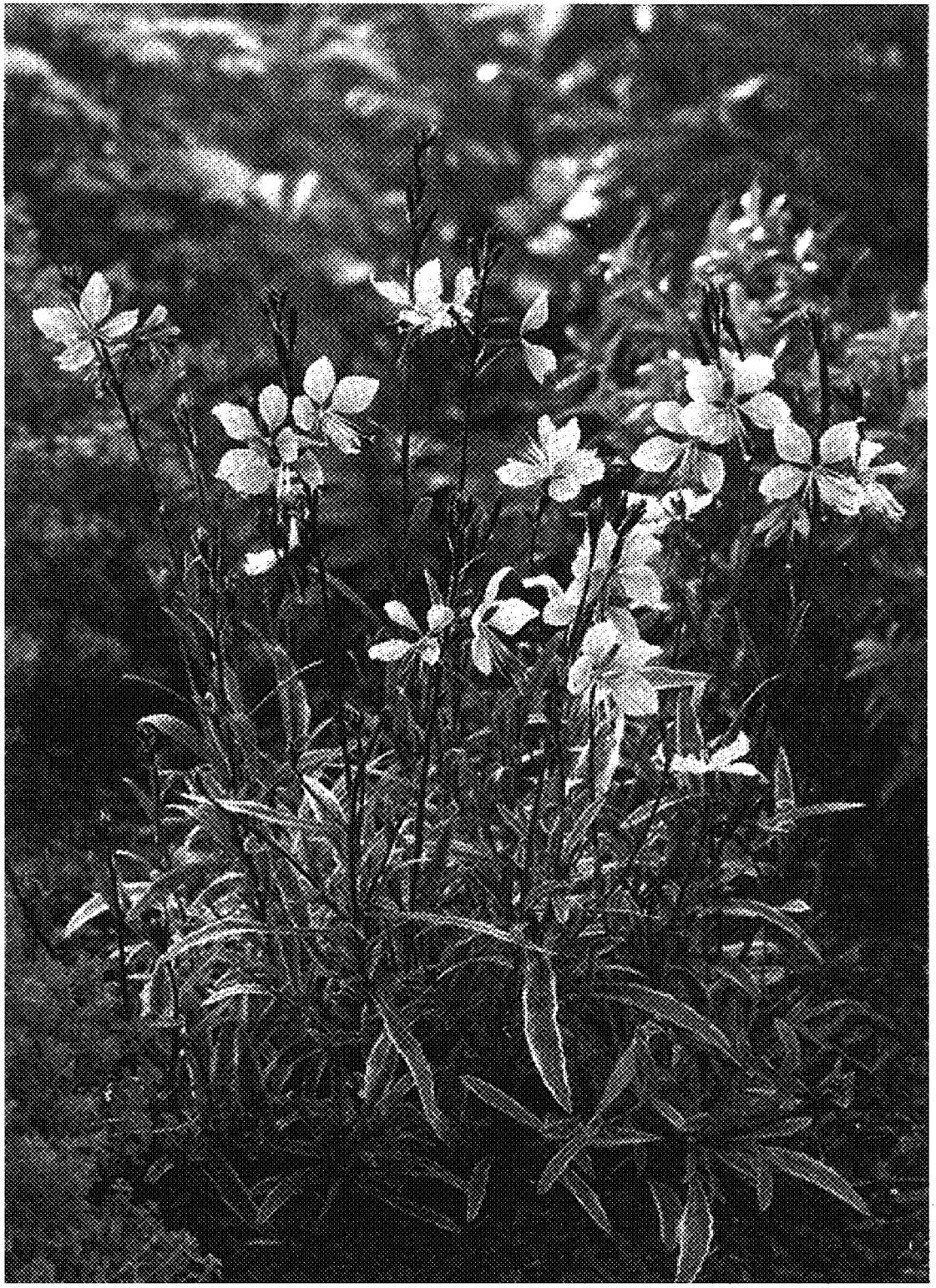
FIG. 2 is a photograph of the spike and flowers of the new variety.
Figure 3:
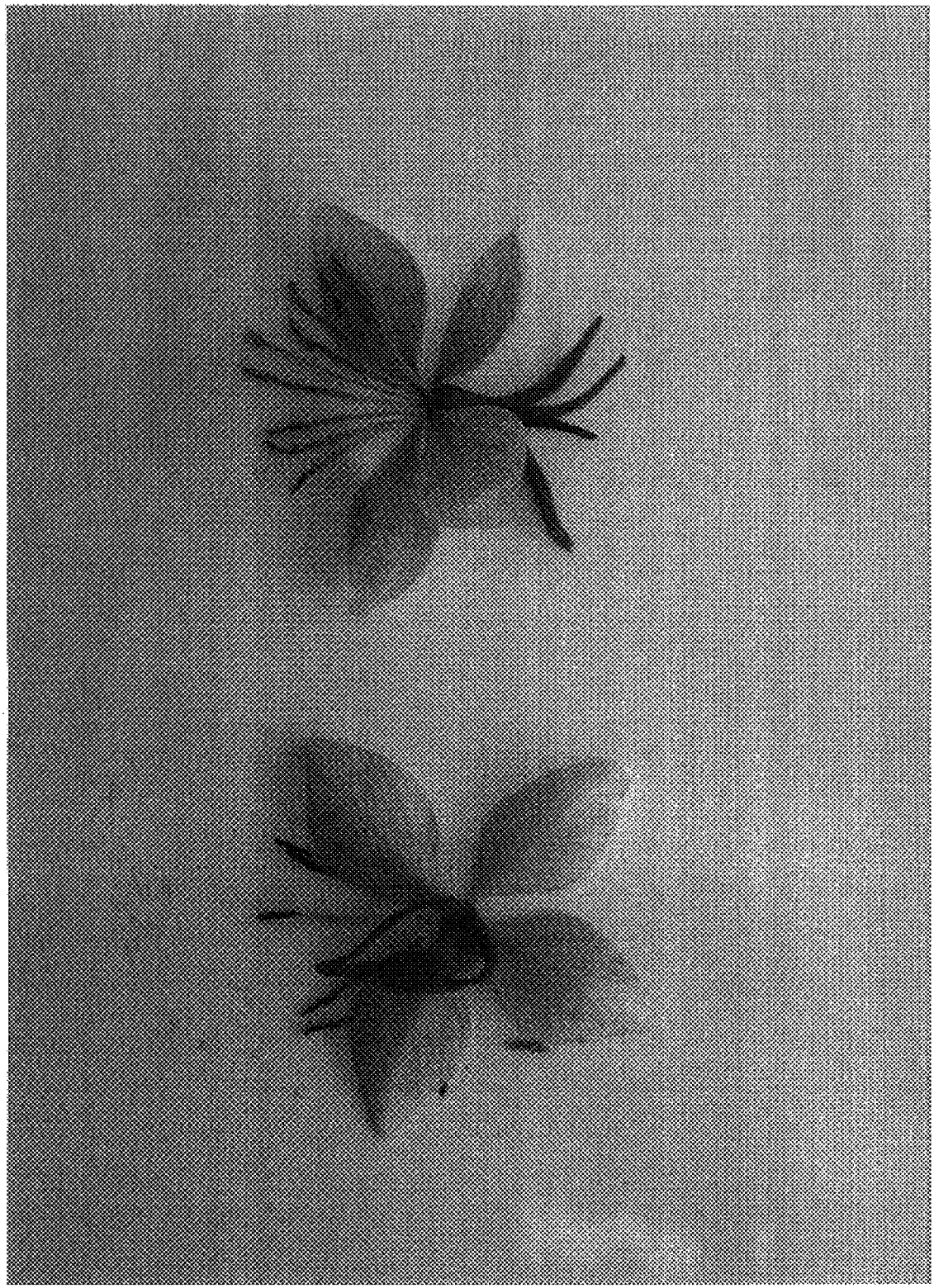
FIG. 3 is a photograph of the flowers of the new variety.
Figure 4:
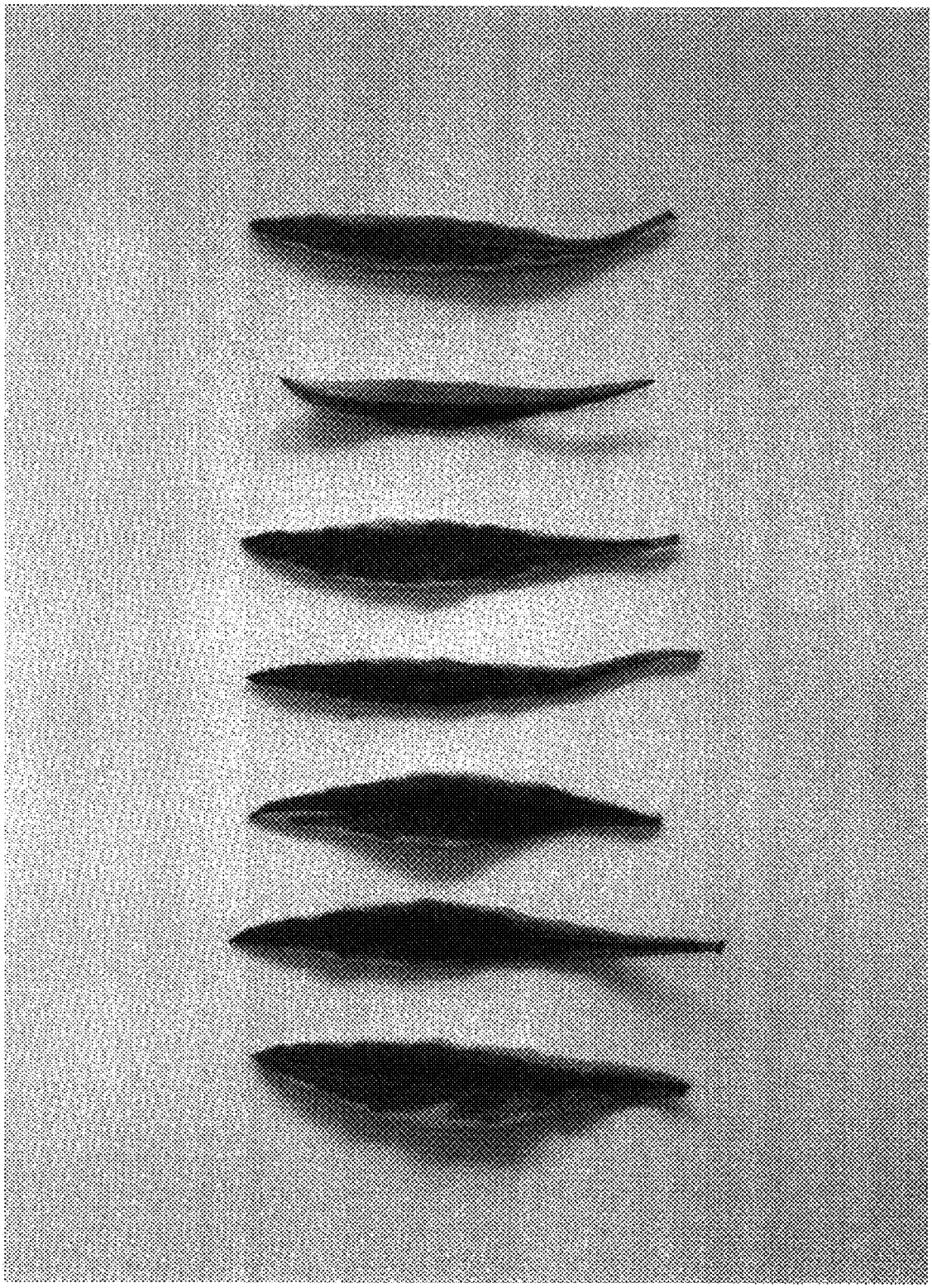
FIG. 4 is a photograph of the leaves of the new variety.

The following detailed description sets forth the characteristics of the new cultivar grown outside in peat-based compost in 17 cm pots with no extra fertilizer in The Netherlands. The data which defines these characteristics was collected by asexual reproductions by cuttings. The color readings were taken in The Netherlands under natural daylight. Color references are primarily to The R.H.S. Colour Chart of The Royal Horticultural Society of London.

PLANT

Time to initiate roots: About 10 days at 22° C.
Time to develop roots: About 30 days at 18° C.
Time to produce a finished flowering plant from a rooted cutting: About 8 weeks in a 9 cm container.
Form: Upright; slightly spreading.
Stem:
- *Diameter.*—Average 3.5 mm.
- *Length.*—Approximately 40 cm from the ground to the flower tip.
- *Color.*—147B and 137B flushed with 59B.
- *Texture.*—Smooth.
- *Pubescence.*—Light.
- *Form.*—Erect.

Height: Blooms are 35–40 cm above soil when grown in a pot and 50 cm above soil when grown in the ground.
Diameter: In a pot, the plant grows to 25 cm in diameter. When grown in the ground, the new variety grows to 35 cm in diameter.
Vigor: Medium.
Branching habit: Free.
Lateral branches:
- *Diameter.*—Approximately 2 mm.
- *Length.*—Between 15 to 25 cm.
- *Internode length.*—10 mm average, but varies slightly.
- *Texture.*—Smooth.
- *Pubescence.*—Light.
- *Color.*—147B and heavily flushed with 59B, especially at the shoot tip.

Foliage:
- *Arrangement.*—Alternate.
- *Size of leaf.*—Length: 6.2 cm average. Width: 0.9 cm average.
- *Shape of leaf.*—Oblanceolate.
- *Shape of apex.*—Acute.
- *Shape of base.*—Attenuate.

*Texture.*—Soft, slightly pubescent.
*Margin type.*—Slightly undulate.
*Pubescence.*—Slight on both upper and lower surfaces.
Color:
*Young leaves.*—
*Upper surface:* The center is 137A and the edge is 9C, with a flushing of 59B.
*Lower surface:* The center is 137B and the edge is 10B, with a flushing of 59B.
*Mature leaves.*—Upper surface: The center is a mixture of 137A and 147A, the edge is 9C, with a flushing of 59B.
*Lower surface:* The center is 137B and the edge is 10B.
Petiole: Sessile: non present.
Veins:
*Color.*—Upper surface: 137C. Lower surface: 137B.

FLOWER

Bud:
*Stage when bud characteristics determined.*—Fully developed.
*Shape.*—Linear.
*Diameter.*—2.5 mm average.
*Length.*—16 mm average.
*Color.*—Main body is 59B with the tip color being 147B.
Natural flowering season: In Northern Europe — from May to late October outside.
Spike:
*Number of flowers.*—Average 23.
*Length.*—23 cm average.
Peduncle:
*Length.*—Approximately 16 mm.
*Diameter.*—Approximately 2 mm.
*Color.*—Between 59A and 59B.
Inflorescence:
*Length.*—15 cm average.
*Diameter.*—4 cm average.
Individual flower:
*Diameter.*—3.2 cm average.
*Depth.*—Approximately 15 mm.
Corolla:
*Form.*—Zygomorphic.
*Petals/lobes.*—Number: 4. Length: 18 mm average. Width: 10 mm average. Shape: Obovate.
*Margin.*—Entire.
*Apex.*—Rounded; obtuse.
*Base.*—Rounded; obtuse.
*Texture and appearance.*—Smooth, matte.
*Color (when opening and fully opened).*—Upper surface: Between 62D and 65D. Lower surface: Between 62D and 65D. Veins: Upper surface: Between 67B and 67C. Lower surface: Between 67B and 67C.
Calyx:
*Form.*—Frequently fused at the tip when the flower is opening. Sometimes they remain fused and/or fail to separate.
*Length.*—15 mm average.
*Diameter.*—2 mm average.
*Sepal number.*—4
*Sepal shape.*—Linear.
*Sepal margin.*—Entire.
*Sepal apex.*—Linear; rounded.
*Sepal texture.*—Smooth, pubescent.
*Sepal size.*—Length: 15 mm average. Width: 2 mm average.
*Sepal color.*—Upper surface: 58A. Lower surface: 58A.
Fragrance: None.
Disease resistance: Good.
Temperature tolerance: Good.
Drought tolerance: Good.
Lasting quality: Flowers last 1–2 days individually.

REPRODUCTIVE ORGANS

Stamens:
*Number.*—8 per flower.
*Filament length.*—14 mm average.
*Anthers.*—Shape: Linear. Length: 3.2 mm. Color: 59A.
Pollen.—Color: 3B. Amount: Plentiful
Pistils:
*Length.*—20 mm average.
*Style.*—Length: 19 mm average. Color: White flushed with 62A.
*Stigma.*—Shape: Four ovals in cruciform. Color: 2C.
Seed: None produced.

I claim:

1. A new and distinct variety of *Gaura lindheimeri* plant substantially as shown and described.

* * * * *